United States Patent [19]
Sulkowski et al.

[11] Patent Number: 4,596,873
[45] Date of Patent: Jun. 24, 1986

[54] 1,4,5,6,7,8-HEXAHYDRO-2-ALKYL-4-ARYL-5-OXO-1,7-NAPHTHYRIDINE-3-CARBOXYLIC ACID AROMATIC ESTERS AND PHARMACEUTICALLY ACCEPTABLE ACID ADDITION SALTS THEREOF USEFUL AS ANTIHYPERTENSIVE AGENTS

[75] Inventors: Theodore S. Sulkowski, Wayne; Paul J. Silver, West Chester; Albert A. Mascitti, Norristown, all of Pa.

[73] Assignee: American Home Products Corporation, New York, N.Y.

[21] Appl. No.: 760,220

[22] Filed: Jul. 29, 1985

[51] Int. Cl.$^4$ ............................................ C07D 471/02
[52] U.S. Cl. .................................................... 546/123
[58] Field of Search ......................................... 546/123

[56]  References Cited
U.S. PATENT DOCUMENTS
4,321,384  3/1982  Sulkowski et al. ................. 546/123

Primary Examiner—Henry R. Jiles
Assistant Examiner—J:. Richter
Attorney, Agent, or Firm—Richard K. Jackson

[57]  ABSTRACT 1,4,5,6,7,8-Hexahydro-2-alkyl-4-aryl-5-oxo-1,7-naphthyridine-3-carboxylic acid aromatic esters and pharmaceutically acceptable acid addition salts thereof are useful antihypertensive agents.

29 Claims, No Drawings

1,4,5,6,7,8-HEXAHYDRO-2-ALKYL-4-ARYL-5-OXO-1,7-NAPHTHYRIDINE-3-CARBOXYLIC ACID AROMATIC ESTERS AND PHARMACEUTICALLY ACCEPTABLE ACID ADDITION SALTS THEREOF USEFUL AS ANTIHYPERTENSIVE AGENTS

BACKGROUND OF THE INVENTION

Pharmacological agents possessing the ability to block cellular transmembrane influx of calcium are capable of suppressing that portion of myocardial or vascular smooth muscle contractility which is dependent upon extracellular calcium. Church et al., Can. J. Physiol. Pharmacol., 58, 254 (1980); Fleckenstein, Calcium and the Heart, P. Harris and L. Opie, eds., Academic Press (1971); Nayler et al., Bas. Res. Cardiol, 76, 1 (1981); Calcium Blockers, S. Flaim and R. Zelis, eds., Urban and Schwartzenberg, (1982).

These pharmacological agents, termed calcium entry blockers, have been proven to be useful in the treatment of hypertension, cardiac arrhythmias, angina pectoris, and coronary artery vasospasm (a possible cause of sudden cardiac death syndrome). Circ. Res., 52, Suppl. I, (1983); Hypertension 5, Suppl. II, (1983). However, a major limitation and deleterious side-effect for use of some of these agents in certain vascular pathologies is the negative inotropism associated with blockade of cardiac sarcolemmal $Ca^{+2}$ channels.

In theory, calcium entry blockers are thought to act by blocking calcium influx through discrete calcium channels (slow channels) in cell membranes. Various tissues exhibit relative differences in sensitivity toward the calcium blocking effect achieved by certain calcium antagonists, theoretically as a result of tissue specific differences in the calcium channels. Acta Pharmacol. Toxicol., 43, 5 (1978); loc. cit. 291 (1978); Microvascular Res., 5, 73 (1973); Am. Rev. Pharmacol. Toxicol., 17, 149 (1977).

A mechanistic difference in $Ca^{+2}$ regulation of contractile activity in vascular smooth muscle and cardiac muscle is believed to exist. In cardiac muscle, $Ca^{+2}$ regulation is primarily thin filament-linked and involves the troponin-tropomyosin system. Stull et al., Handbook of Physiology, The Cardiovascular System, vol. 1, R. Berne, N. Sperelakis and S. Geiger, eds., American Physiological Society (1979); Solaro, Calcium Blockers, ibid., supra. In vascular smooth muscle, regulation is primarily dependent upon $Ca^{+2}$-calmodulin mediated myosin light chain phosphorylation. Hartshorne et al., Handbook of Physiology, The Cardiovascular System, vol. 2., Bohr, Somlyo and Sparks, eds., American Physiological Society (1982); Silver et al., Calcium Blockers, ibid., supra.

Calcium antagonists which antagonize the effects of $Ca^{+2}$ by inhibiting $Ca^{+2}$-calmodulin mediated myosin light chain phosphorylation would be more specific for vascular smooth muscle than cardiac muscle and would be less liable to produce negative inotropic cardiac contraction.

U.S. Pat. Nos. 4,321,384, granted Mar. 31, 1982, and 4,365,063, granted Dec. 21, 1982, disclose hexahydro-2-alkyl-4-aryl-5-oxo-1,7-naphthyridine-3-carboxylic acid esters in which the alcohol derived portion of the ester is an alkyl, alkoxyalkyl, trifluoromethylalkyl or aminoalkyl moiety.

RELATED APPLICATIONS

Copending U.S. application Ser. No. 595,168 claims hexahydro-1,7-naphthyridine derivatives in which the nitrogen in 7-position has been variously modified. The compounds disclosed in Ser. No. 595,168 are less potent antihypertensive agents when administered orally than the modified esters of the following disclosure.

DESCRIPTION OF THE INVENTION

In accordance with this invention there is provided a group of 1,4,5,6,7,8-hexahydro-2-alkyl-4-aryl-5-oxo-1,7-naphthyridine-3-carboxylic acid ester derivatives and pharmaceutically acceptable acid addition salts thereof, which are useful antihypertensive agents. The compounds of this invention differ structurally from the compounds of the U.S. patents cited, supra, in the presence of an aromatic group in the alcohol moiety of the ester grouping. In addition, the compounds disclosed herein differ in their pharmacological profile in that they are more vascular specific as opposed to cardiac specific antihypertensive agents and they present less toxic liability. The compounds of this invention also antagonize arterial actin-myosin interactions and $Ca^{+2}$-calmodulin dependent myosin light chain phosphorylation. Thus, the compounds of this invention are aryloxyalkyl esters, alkoxy(aryl)alkyl esters, arylalkyl esters, benzodioxan-2-alkyl esters or benzoalkyleneoxid-2-ylalkyl esters. The aromatic ring of the ester may be substituted by from one to five halo groups (e.g., —Cl, —Br, —F), and/or from 1 to 3 groups, —$CF_3$, alkyl of 1 to 6 carbon atoms or alkoxy of 1 to 6 carbon atoms. The alkyl moiety of the ester may be straight or branched chain and contain from two to six carbon atoms in its linear portion.

More specifically, the antihypertensive agents of this invention are compounds of the formula:

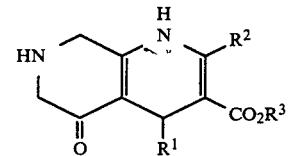

in which
$R^1$ is tetra- or penta- chloro, bromo or fluoro-phenyl or

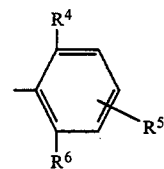

where
$R^4$ and $R^5$ are, independently, hydrogen, alkyl of 1 to 6 carbon atoms, halo, trifluoromethyl, alkoxy of 1 to 6 carbon atoms, alkylthio of 1 to 6 carbon atoms, cyano or nitro; and
$R^5$ is hydrogen, alkyl of 1 to 6 carbon atoms, halo, trifluoromethyl, cyano or nitro;
$R^2$ is alkyl of 1 to 6 carbon atoms; and
$R^3$ is

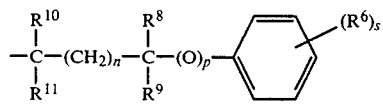

where

R$^6$ is, independently, hydrogen, —Cl, —Br, —F, and no more than three of the groups —CF$_3$, alkyl of 1 to 6 carbon atoms or alkoxy of 1 to 6 carbon atoms;

R$^8$ is hydrogen, alkyl of 1 to 6 carbon atoms or alkoxy of 1 to 6 carbon atoms;

R$^9$, R$^{10}$ and R$^{11}$ are, independently, hydrogen or alkyl of 1 to 6 carbon atoms;

n is one of the integers 0, 1, 2, 3 or 4;

s is one of the integers 1, 2, 3, 4 or 5;

p is one of the integers 0 or 1, with the proviso that when R$^8$ is alkoxy, p is 0;

or R$^3$ is

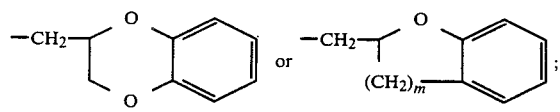

where m is one of the integers 1, 2, 3 or 4;

or a pharmaceutically acceptable salt thereof.

With reference to the above-described compound genus, the preferred variables from the standpoint of production economics and activity profile are those in which the group R$^1$ contains halogen substituents and R$^3$ is an aryloxyalkyl group devoid of chiral centers. Thus, the preferred subgenus is a group of compounds of the formula:

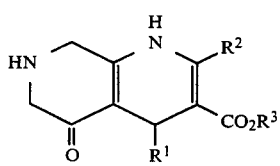

in which

R$^1$ is tetra- or penta- chloro, bromo or fluoro-phenyl or

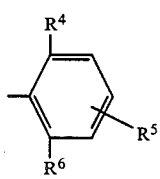

where R$^4$ and R$^6$ are halo and R$^5$ is defined above;

R$^2$ is alkyl of 1 to 6 carbon atoms; and

R$^3$ is

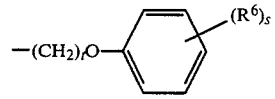

where t is one of the integers 2, 3, 4, 5, or 6 and R$^6$ and s are defined above;

or a pharmaceutically acceptable salt thereof.

A second subgeneric group of compounds of this invention may be depicted as:

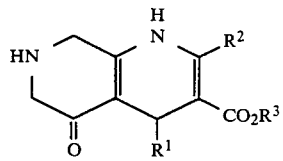

in which R$^1$ and R$^2$ are as defined in the generic statement of the invention, and R$^3$ is

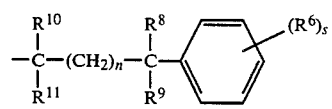

where n, s, R$^6$, R$^9$, R$^{10}$ and R$^{11}$ are as defined in the genus and R$^8$ is alkoxy of 1 to 6 carbon atoms; or a pharmaceutically acceptable salt thereof.

The aromatic alkylene oxide subgenus of compounds present the subgenus:

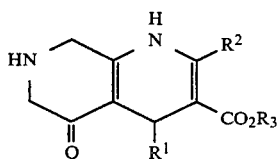

in which R$^1$ and R$^2$ are as defined in the generic statement of the invention and R$^3$ is

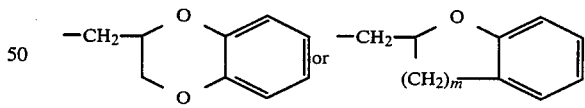

where m is one of the integers 1, 2, 3 or 4; or a pharmaceutically acceptable salt thereof.

The compounds of this invention may be prepared by reaction of 1-benzyl-3-hydroxy-5-oxo-tetrahydropyridine, an appropriate ester of acetoacetic acid, an appropriately substituted benzaldehyde and an ammonia source such as ammonium acetate. The reaction is carried out in an alcohol, preferably methanol at elevated temperature (e.g. reflux) for from two to about eighteen hours, preferably about six hours. The product is subjected to catalytic hydrogenation, preferably in the presence of a mineral acid, to remove the benzyl protecting group present on the nitrogen atom in 7-position. Thus:

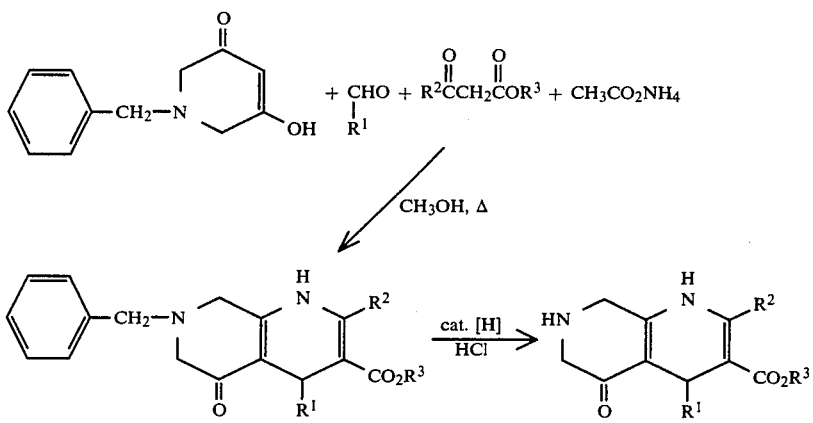

The appropriately substituted benzaldehydes are either commercially available or are prepared by standard procedures. The preparation of 2,3-dichloro-6-fluorobenzaldehyde is illustrated in Example 24, infra. The acetoacetic acid ester derivatives are conventionally prepared by reaction of diketene with the appropriately substituted alcohol. The procedure is illustrated by preparation of 2-phenoxyethyl acetoacetate:

Diketene (84 g) was added dropwise with stirring to 140 g of 2-phenoxyethanol heated at 100° C. After the addition was completed, the reaction mixture was refluxed for an additional 22 hours. The reaction mixture was fractionally distilled to obtain 90.6 g of 2-phenoxyethyl acetoacetate, BP 140°–145° C./0.3 mm.

Analysis for: $C_{12}H_{14}O_4$. Calculated: C, 64.85; H, 6.35. Found: C, 64.45; H, 6.48.

In a similar manner, diketene was reacted with 2-hydroxymethyl-1,4-benzodioxin-2-ylmethyl acetoacetate, BP 120°–140° C./0.05 mm (flash distillation).

In a similar manner, diketene was reacted with 1-phenoxy-2-propanol to obtain 1-methyl-2-(phenoxy)ethyl acetoacetate, BP 115°–122° C./0.05–0.1 mm.

In a similar manner, diketene was reacted with (±)-2-methoxy-2-phenylethanol to obtain 2-methoxy-2-phenylethyl acetoacetate, BP 115°–120° C./0.2 mm.

In a similar manner diketene was reacted with 2-(2,3-dichlorophenoxy)-ethanol to obtain 2-(2,3-dichlorophenoxy)ethyl acetoacetate, BAP 150°–170° C./0.25 mm (flash distillation).

In a similar manner, diketene was reacted with 4-phenoxybutanol to obtain 4-phenoxybutyl acetoacetate, BP 115°–125° C./0.25 mm (flash distillation).

In a similar manner, diketene was reacted with 2-cyclohexyloxyethanol to obtain 2-cyclohexyloxyethyl acetoacetate, BP 115°–120° C./0.5 mm (flash distillation).

The compounds of this invention may be produced in step-wise manner with isolation of intermediates, if desired, rather than by the preferred one pot technique discussed, supra. In all of these procedures the reactions involve a Michael addition—cyclic condensation of an oxoenamine or precursors thereof to a Knoevenagel condensation product. Thus, by selection of the proper reactants which are either commercially available or prepared by standard procedures, the following procedures are applicable and involve the separate preparation of the appropriately substituted aminocrotonate, amino ketone or appropriately substituted benzylidene acetoacetic ester:

Amino Crotonate

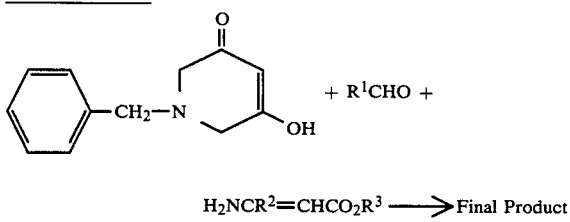

Amino Ketone

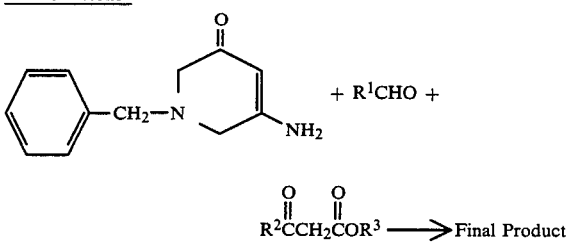

Benzylidene Acetoacetic Ester

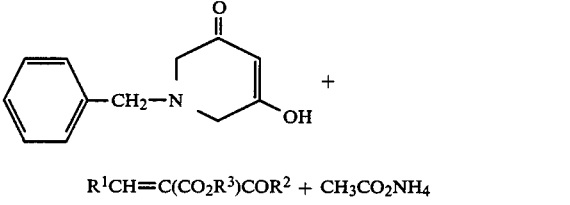

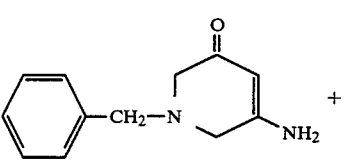

Benzylidene Diketone

-continued

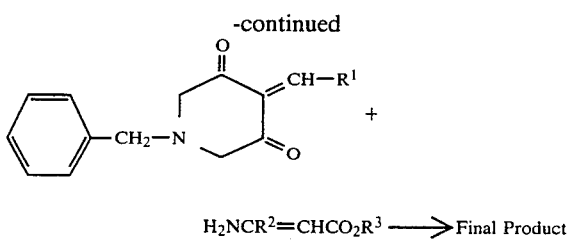

H$_2$NCR$^2$=CHCO$_2$R$^3$ ⟶ Final Product

Thus, in a generic process sense the compounds of this invention are produced by adding, with cyclic condensation (a Michael addition-cyclization), an appropriately substituted oxoenamine, or precursors thereof, to a Knoevenagel condensation product of an appropriately substituted aldehyde and an alkanoylacetic acid ester or a 1-benzyl-3-hydroxy-5-oxo-2,3,4,6-tetrahydropyridine. The N-benzyl protecting group is, of course, ultimately removed by hydrogenolysis.

The pharmaceutically acceptable salts of the antihypertensive agents of this invention are prepared directly by neutralization of the free base or by metathetical displacement. The physiologically acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicylic, lactic, naphthalenesulfonic acid, and the like.

The compounds of this invention were initially shown to exhibit Ca$^{+2}$ antagonism in rabbit aortic smooth muscle following a modified procedure from that described by Brockaert et al., Eur. J. Pharmacol., 53, 281 (1979) whereby transverse strips (10 mm×2.5 mm) from the thoracic aorta were cut and suspended vertically in a jacketed (37° C.-50 ml volume) organ bath in physiological saline solution (PSS) aerated with 95% O$_2$/5% CO$_2$. The composition of PSS was as follows (mM): NaCl 112, KCl 5, NaHCO$_3$ 25, KH$_2$PO$_4$ 1, MgSO$_4$ 1.2, CaCl$_2$ 2.5, dextrose 10. The lower end of each tissue strip was attached to a fixed post and the upper end to a Statham UC-4 transducer. Changes in force development were recorded on a Beckman Dynograph Polygraphic Recorder.

Following equilibration, the muscles were contracted in a depolarizing solution of PSS in which 100 mM KCl was substituted for an equimolar concentration of NaCl. Following attainment of steady-state isometric force (20 min.), the test compound was added to afford a final concentration of 1×10$^{-5}$M. The inhibitory effect, expressed as percent relaxation, was determined from the mean of two experiments twenty minutes after the addition of the compound being tested.

The potential for detrimental cardiac depressant (negative inotropic) effects of the compounds of this invention was assessed in isolated paced intact rabbit atria. Left and right atria (with nodal tissue excised) were suspended vertically in a jacketed (30° C.) organ bath containing 50 ml of PSS and aerated with 95% O$_2$/5% CO$_2$. Muscles (N=5-9/compound) were stimulated at a frequency of 3 Hz with a WPI stimulator for a 60 minute equilibration period. Changes in isometric force were recorded as described for the aortic smooth muscle experiments, supra. Following equilibration, the test compound (or as a control, the ethanol vehicle) was added to the organ bath in a cumulative manner from doses ranging from 10$^{-9}$M to 10$^{-5}$M (10$^{-5}$M was the maximum dose which could be attained due to the depressant effect of ethanol) and effects on developed isometric force were determined. Results are expressed as the concentration of calcium antagonist which produces 25% inhibition of isometric force (IC$_{25}$).

Known calcium entry blockers produced significant cardiac depression in this model. Verapamil (IC$_{25}$=6×10$^{-8}$M), nifedipine (IC$_{25}$=5×10$^{-8}$M), nitrendipine (IC$_{25}$=3.5×10$^{-7}$M) and felodipine (IC$_{25}$=8×10$^{-7}$M) all produced direct negative inotropism. However, the known calmodulin inhibitor, W-7, produced less than 20% inhibition at the highest concentration (10$^{-5}$M) tested.

The hypotensive in vivo effect of the compounds of this invention was determined by measuring changes in the systolic blood pressure of spontaneously hypertensive rats with a Decker Caudal Plethysmograph. The compound being tested was administered to a group of 4 rats and their systolic pressure was determined prior to and at 1.5 and 4 hours after compound administration. Initial testing was done by oral administration of the compound. Results (mmHg) are expressed as decreases in systolic blood pressure.

The compounds were also shown, unlike nifedipine, verapamil and nitrendipine, and like the calmodulin antagonist W-7, to antagonize arterial actin-myosin interactions and Ca$^{+2}$-calmodulin dependent myosin light chain phosphorylation and subsequent contractile protein function when studied in accordance with the procedures of Silver et al., J. Pharmacol. Exp. Therap., 230, No. 1, 141-148 (1984). The data reported herein was obtained at a six minute time-point rather than the 1.5, 5 and 12 minute time points indicated in the superprecipitation assay of the Silver et al. paper.

Thus, these data establish the compounds of this invention as Ca$^{+2}$ antagonists which are useful as antihypertensive agents functioning more at the vascular level than other known Ca$^{+2}$ entry blockers.

Based upon the activity profile elicited by the compounds of this invention in the above-described standard scientifically recognized test models, the compounds are established as hypotensive agents useful in the treatment of hypertension and conditions characterized by constrictive blood flow in coronary arteries. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from 1 to about 50 milligrams per kilogram host body weight to be administered in single or plural doses as needed to obtain the desired hypotensive response. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavor or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention.

After each example, and Ca$^{+2}$ antagonist activity of the compound is presented in terms of percent relaxation of aortic tissue (P.R.) at 10$^{-5}$M concentration. Also, the IC$_{25}$ data, where determined in atrial tissue, is presented for comparison purposes with that of standard Ca$^{+2}$ antagonists noted, supra, and to show that the compounds of this invention are operating more through the vascular smooth muscle regulatory mechanism than the known Ca$^{+2}$ entry blockers. Inhibition of superprecipitation (Antag. of Actin-Myosin interaction) is expressed as percent inhibition (mean±standard error of the mean for at least 3 separate experiments) at a compound concentration. In the same manner, inhibition of myosin light chain phosphorylation (Antag. of MLCP) is expressed as a percent inhibition at a compound concentration. Similarly, the antihypertensive activity is reported in terms of millimeters mercury (mmHg) systolic blood pressure (B.P.) reduction at the stated time post 50 mg/kg oral dosing or other dosing as indicated.

EXAMPLE 1

4-(2,3-Dichlorophenyl)-1,4,5,6,7,8-hexahydro-2-methyl-5-oxo-1,7-naphthyridine-3-carboxylic acid 2-methoxy-2-phenylethyl ester A mixture of 15.2 g of 1-benzyl-3-hydroxy-5-oxo-2,3,4,6-tetrahydropyridine hydrate, 17.7 g of 2-methoxy-2-phenylethyl acetoacetate, 13.1 g of 2,3-dichlorobenzaldehyde, 11.5 g of ammonium acetate and 300 ml of methanol was refluxed for 6 hours. The solvent was removed in vacuo and the residue was slurried with ethyl acetate and filtered. The solid was dissolved in methylenechloride, extracted with water, then dried over magnesium sulfate. The methylene chloride was evaporated and the residue was slurried with diethyl ether and filtered to obtain 10.2 g of solid, m.p. 220°-2° C. Conversion to the hydrochloride afforded 10.3 g of 4-(2,3-dichlorophenyl)-1,4,5,6,7,8-hexahydro-2-methyl-5-oxo-7-(phenylmethyl)-1,7-naphthyridine-3-carboxylic acid 2-methoxy-2-phenylethyl ester hydrochloride, m.p. 217° C. dec.

Analysis for: $C_{32}H_{30}N_2Cl_2O_4$.HCl. Calculated: C, 62.60; H, 5.09; N, 4.56; Cl, 17.33. Found: C, 62.67; H, 5.10; N, 4.54; Cl, 17.66.

The above hydrochloride (7.8 g), 200 ml of methanol, 10 ml of concentrated hydrochloric acid, and 0.5 g of 10% palladium on charcoal were shaken with hydrogen (40 psig initial pressure) for 6 hours. The catalyst was separated and solvent was evaporated in vacuo. Ethanol was added to the residue and re-evaporated (3 times). The residue was slurried with diethyl ether and filtered. The solid was recrystallized from isopropanol-diethyl ether to obtain 4.7 g of the title compound as the hydrochloride, m.p. 150°-3° C.

Analysis for: $C_{25}H_{24}N_2Cl_2O_4$.HCl. Calculated: C, 57.32; H, 4.81; N, 5.35; Cl, 20.30. Found: C, 57.49; H, 4.92; N, 5.68; Cl, 19.63.

P.R.=32.

IC$_{25}$=1×10$^{-5}$M.

Antag. of Actin-Myosin-100 μM=83±3%; 50 μM=75±3%; 25 μM=43±2%.

Antag. of MLCP-100 μM=76±2%; 50 μM=66%; 25 μM=38±3%.

B.P.-dose 50 mg/kg= −53 mm at 1.5 hours; −30 mm at 4 hours.

EXAMPLE 2

1,4,5,6,7,8-Hexahydro-2-methyl-5-oxo-4-(pentafluorophenyl)-1,7-naphthyridine-3-carboxylic acid 2-phenoxyethyl ester Methanol (300 ml), 15.2 g of 1-benzyl-3-hydroxy-5-oxo-2,3,4,6-tetrahydropyridine hydrate, 16.6 g of phenoxyethyl acetoacetate, 14.7 g of pentafluorobenzaldehyde and 11.5 g of ammonium acetate were mixed and refluxed for 6 hours. A precipitate formed during this period. After cooling to room temperature, the mixture was filtered to obtain 20 g of solid, m.p. 237°-9° C. dec. Conversion to the hydrochloride afforded 18.5 g of 1,4,5,6,7,8-hexahydro-2-methyl-5-oxo-4-(pentafluorophenyl)-7-(phenylmethyl)-1,7-naphthyridine-3-carboxylic acid 2-phenoxyethyl ester hydrochloride, m.p. 208°-210° C.

Analysis for: $C_{31}H_{25}N_2F_5O_4$.HCl. Calculated: C, 59.95; H, 4.22; N, 4.51; Cl, 5.71. Found: C, 60.16; H, 4.38; N, 4.82; Cl, 5.42.

A mixture of 16.4 g of the above hydrochloride, 200 ml of methanol, 5 ml of concentrated hydrochloric acid, 15 ml of water and 0.5 g of 10% palladium on carbon was shaken with hydrogen at an initial pressure of 50 psig. After shaking 18 hours, the catalyst was separated and the solution was evaporated to dryness in vacuo. The residue was slurried with ethanol and re-evaporated (3 times). The solid was separated and dissolved in boiling ethanol. The solution was evaporated to a small volume and diluted with diethyl ether. The precipitate was separated and dried to obtain 8.7 g of the title compound as the hydrochloride salt, m.p. 230° C. dec.

Analysis for: $C_{24}H_{19}N_2F_5O_4$.HCl. Calculated: C, 54.30; H, 3.80; N, 5.28; Cl, 6.68. Found: C, 54.05; H, 3.82; N, 5.19; Cl, 6.71.

P.R.=71.

IC$_{25}$=1×10$^{-6}$M.

Antag. of Actin-Myosin-100 μM=72±2%; 50 μM=58±4%; 25 μM=28±2%.

Antag. of MLCP-100 μM=69±3%; 50 μM=54±4%; 25 μM=24±3%.

B.P.-dose 10 mg/kg= −39 mm at 1.5 hours; −51 mm at 4 hours.

EXAMPLE 3

(−)-1,4,5,6,7,8-Hexahydro-2-methyl-5-oxo-4-(pentafluorophenyl)-1,7-naphthyridine-3-carboxylic acid 2-phenoxyethyl ester 1,4,5,6,7,8-Hexahydro-2-methyl-5-oxo-4-(pentafluorophenyl)-1,7-naphthyridine-3-carboxylic acid 2-phenoxyethyl ester (30.3 g), 14.4 g of (+) 2'-methyltartranilic acid and 1 liter of acetonitrile were heated to solution then left at room temperature for 18 hours. The precipitate was separated and the filtrate was set aside for later work-up. The solid was recrystallized twice from acetonitrile to obtain 11.5 g of 2'-methyltartranilic acid salt, $[\alpha]_D^{26}$= −85.24 [0.725; MeOH]. The salt was converted to 7.4 g of base $[\alpha]_D^{26}$= −181.96° [0.51; MeOH]. The base was suspended in methanol and treated with hydrogen chlorine. The solution was evaporated to dryness in vacuo and the residue was dissolved in ethanol and re-evaporated (2 times). The residue was triturated with diethyl ether and filtered to obtain 7.3 g of the title compound as the hydrochloride, $[\alpha]_D^{26}$= −155.89° [0.705; MeOH].

Analysis for: $C_{24}H_{19}N_2F_5O_4.HCl$. Calculated: C, 54.30; H, 3.80; N, 5.28; Cl, 6.68. Found: C, 54.25; H, 3.73; N, 5.14; Cl, 6.51.

P.R.=56.

$IC_{25} > 1 \times 10^{-5}M$.

Antag. of Actin-Myosin-100 $\mu M=76\%$; 50 $\mu M=65\%$.

Antag. of MLCP-100 $\mu M=70\%$; 50 $\mu M=57\%$.

B.P.-dose 25 mg/kg= −6 mm at 1.5 hours; −14 mm at 4 hours.

EXAMPLE 4

(+)-1,4,5,6,7,8-Hexahydro-2-methyl-5-oxo-4-(pentafluorophenyl)-1,7-naphthyridine-3-carboxylic acid 2-phenoxyethyl ester The original filtrate from Example 3 was evaporated to dryness and the residue was converted to 18.2 g of base by treatment with saturated sodium carbonate solution. The recovered base and 8.7 g of (−)-2′-methyltartranilic acid were dissolved in 370 ml of boiling acetonitrile. After standing at room temperature for 18 hours, the precipitate was separated and recrystallized twice from acetonitrile to obtain 13.5 g of 2′-methyltartranilic acid salt, $[\alpha]_D^{25}=+87.33°$ [0.656; MeOH]. The salt was converted to 8.9 g of base, $[\alpha]_D^{26}=+182.04°$ [0.635; MeOH]. The base was converted to the hydrochloride as in the previous example to obtain 8.5 g of the title compound as the hydrochloride, $[\alpha]_D^{26}=+158.71°$ [0.62; MeOH].

Analysis for: $C_{24}H_{19}N_2F_5O_4.HCl$. Calculated: C, 54.30; H, 3.80; N, 5.28; Cl, 6.68. Found: C, 54.08; H, 3.79; N, 5.22; Cl, 6.56.

P.R.=61.

$IC_{25}=8\times 10^{-7}M$.

Antag. of Actin-Myosin-100 $\mu M=71\%$; 50 $\mu M=38\%$.

Antag. of MLCP-100 $\mu M=67\%$; 50 $\mu M=37\%$.

B.P.-dose 25 mg/kg= −58 mm at 1.5 hours; −78 mm at 4 hours.

EXAMPLE 5

1,4,5,6,7,8-Hexahydro-2-methyl-5-oxo-4-(pentafluorophenyl)-1,7-naphthryridine-3-carboxylic acid 2-methoxy-2-phenylethyl ester A solution of 15.5 g of 1-benzyl-3-hydroxy-5-oxo-2,3,4,6-tetrahydropyridine hydrate, 14.7 g of pentafluorobenzaldehyde, 17.7 g of 2-methoxy-2-phenylethyl acetoacetate, 11.6 g of ammonium acetate and 300 ml of methanol was heated at reflux for 8 hours. After cooling, the mixture was filtered to obtain 22.5 of solid. Recrystallization from ethanol afforded 17.3 g of 1,4,5,6,7,8-hexahydro-2-methyl-5-oxo-4-(pentafluorophenyl)-7-(phenylmethyl)-1,7-naphthyridine-3-carboxylic acid 2-methoxy-2-phenylethyl ester, mp. 220°-2° C.

Analysis for: $C_{32}H_{27}N_2F_5O_4$. Calculated: C, 64.20; H, 4.55; N, 4.68. Found: C, 63.98; H, 4.49; N, 4.67.

A mixture of 16.9 g of the above solid, 250 ml of methanol, 2 ml of concentrated hydrochloric acid and 1 g of 10% palladium on carbon was shaken with hydrogen (initial pressure 40 psig) for 13 hours. The catalyst was separated and the solution was evaporated to dryness in vacuo. The residue was treated with methylenechloride and saturated sodium bicarbonate solution. The methylenechloride solution ws dried over magnesium sulfate, then evaporated to dryness. The residue was dissolved in 30 ml of ethyl acetate, filtered, and diluted with 30 ml of pentane. Filtration afforded 8.3 g of solid, mp. 175°-180° C. An ethanol solution of 2.3 g of this solid was treated with an excess of ethanolic hydrogen chloride. The solution was evaporated to dryness. The residue was reprecipitated from ethyl acetate-pentane to obtain 2 g of the title compound as the hydrochloride, hemi-hydrate, mp. 180°-5° C. dec.

Analysis for: $C_{25}H_{21}N_2F_5O_4.HCl.\frac{1}{2}H_2O$. Calculated: C, 54.20; H, 4.20; N, 5.06; Cl, 6.40; $H_2O$, 1.60. Found: C, 54.29; H, 4.00; N, 5.02; Cl, 6.53; $H_2O$, 1.96.

P.R.=71.

$IC_{25}=1\times 10^{-6}M$.

Antag. of Actin-Myosin-100 $\mu M=75\pm 4\%$; 50 $\mu M=50\pm 5\%$; 25 $\mu M=20\pm 5\%$.

Antag. of MLCP-100 $\mu M=70\pm 3\%$; 50 $\mu M=48\pm 2\%$; 25 $\mu M=21\pm 3\%$.

B.P.-dose 25 mg/kg= −60 mm at 1.5 hours; −72 mm at 4 hours;

10 mg/kg= −41 mm at 1.5 hours; −68 mm at 4 hours;

5 mg/kg= −44 mm at 1.5 hours; −38 mm at 4 hours.

EXAMPLE 6

1,4,5,6,7,8-Hexahydro-2-methyl-5-oxo-4-(pentafluorophenyl)-1,7-naphthyridine-3-carboxylic acid (R)-2-methoxy-2-phenylethyl ester A mixture of 23 g of 1-benzyl-3-hydroxy-5-oxo-2,3,4,6-tetrahydropyridine hydrate, 21.9 g of pentafluorobenzaldehyde, 26.3 g of R(−)-2-methoxy-2-phenylethyl acetoacetate, 17.3 g of ammonium acetate and 200 ml of methanol was heated to reflux. Solid began to precipitate within 20 minutes. After five hours, the mixture was cooled and filtered. The solid was recrystallized from ethanol to obtain 25 g of material, mp. 221°-2° C., $[\alpha]_D^{26}=10.27$ [0.935; MeOH]. The base was converted to the hydrochloride and recrystallized from acetonitrile to obtain 17.5 g of 1,4,5,6,7,8-hexahydro-2-methyl-5-oxo-4-(pentafluorophenyl)-7-(phenylmethyl)-1,7-naphthridine-3-carboxylic acid (R)-2-methoxy-2-phenylethyl ester hydrochloride, mp. 210°-4° C. dec.; $[\alpha]_D^{25}=-18.24°$ [1.025; MeOH].

Analysis for: $C_{32}H_{27}N_2F_5O_4.HCl$. Calculated: C, 60.52; H, 4.44; N, 4.41; Cl, 5.58. Found: C, 60.73; H, 4.46; N, 4.51; Cl, 5.38.

Fourteen grams of the above solid, 200 ml of methanol, 7 ml of concentrated hydrochloric acid, 10 ml of water and 1 g of 10% palladium on carbon were shaken with hydrogen at an initial pressure of 50 psig. After 4 hours, the catalyst was separated and the solution was evaporated to dryness in vacuo. The residue was stirred with ethyl acetate and saturated sodium carbonate solution. The ethyl acetate portion was dried over magnesium sulfate and evaporated to dryness. The residue was crystallized from 50 ml of diethyl ether to obtain 8.5 g of solid, mp. 159°-161° C.; $[\alpha]_D^{25}=-19.44°$ [1.065; MeOH]. The solid was dissolved in ethanol and saturated with hydrogen chloride. The solution was treated with charcoal, filtered, and evaporated to dryness. The residue was reprecipitated from methylene chloride-hexane to obtain 6.8 g of the title compound as the hydrochloride, $[\alpha]_D^{25}=-21.16$ [1.12; MeOH].

Analysis for: $C_{25}H_{21}N_2F_5O_4.HCl$. Calculated: C, 55.10; H, 4.07; N, 5.14; Cl, 6.51. Found: C, 54.92; H, 4.20; N, 4.99; Cl, 6.11.

P.R.=71.

$IC_{25}=6\times 10^{-7}M$.

Antag. of Actin-Myosin-100 μM=74%; 50 μM=64%.

Antag. of MLCP-100 μM=70%; 50 μM=56%.

B.P.-dose 10 mg/kg= −56 mm at 1.5 hours; −49 mm at 4 hours.

EXAMPLE 7

1,4,5,6,7,8-Hexahydro-2-methyl-5-oxo-4-(pentafluorophenyl)-1,7-naphthyridine-3-carboxylic acid (S)-2-methoxy-2-phenylethyl ester A mixture of 23 grams of 1-benzyl-3-hydroxy-5-oxo-2,3,4,6-tetrahydropyridine hydrate, 21.9 g of pentafluorobenzaldehyde, 26.3 g of S(+)-2-methoxy-2-phenylethyl acetoacetate, 17.3 g of ammonium acetate and 200 ml of methanol was heated to reflux. Solid began to precipitate within 20 minutes. After 4 hours, the mixture was cooled and filtered. The precipitate was recrystallized from ethanol to obtain 22 g of solid, m.p. 218°–221° C.; $[\alpha]_D^{25.5}= +10.14°$ [1.065; CHCl$_3$]. The base was converted to the hydrochloride and recrystallized from acetonitrile to obtain 15.5 g of 1,4,5,6,7,8-hexahydro-2-methyl-5-oxo-4-(pentafluorophenyl)-7-(phenylmethyl)-1,7-naphthyridine-3-carboxylic acid (S)-3-methoxy-2-phenylethyl ester hydrochloride, mp. 210°–4° C. dec.; $[\alpha]_D^{25}= +20.94$ [1.27; MeOH].

Analysis for: $C_{32}H_{27}N_2F_5O_4 \cdot HCl$. Calculated: C, 60.52; H, 4.44; N, 4.41; Cl, 5.58. Found: C, 60.80; H, 4.41; N, 4.37; Cl, 5.47.

Thirteen grams of the above hydrochloride, 200 ml of methanol, 7 ml of concentrated hydrochloric acid, 10 ml of water and 1 g of 10% palladium on carbon were shaken with hydrogen at an initial pressure of 50 psig. After 4 hours, the catalyst was separated and the solution was evaporated to dryness in vacuo. The residue was dissolved in ethyl acetate and shaken with saturated sodium carbonate solution. The ethyl acetate portion was dried over magnesium sulfate, then evaporated to dryness. The residue was crystallized from 50 ml of diethyl ether to obtain 6.2 g of solid, mp. 158°–160° C.; $[\alpha]_D^{25}= +20.10°$ [1.025; MeOH]. The solid was dissolved in ethanol and saturated with hydrogen chloride. The solution was treated with charcoal, filtered and evaporated to dryness. The residue was reprecipitated twice from methylenechloride-hexane to obtain 4.5 g of the title compound as the hydrochloride, monohydrate, $[\alpha]_D^{26}= +21.71°$ [1.055; MeOH].

Analysis for: $C_{25}H_{21}N_2F_5O_4 \cdot HCl \cdot H_2O$. Calculated: C, 53.34; H, 4.30; N, 4.98; Cl, 6.30. Found: C, 53.37; H, 4.13; N, 4.95; Cl, 6.23.

P.R.=68.

IC$_{25}$=6.5×10$^{-6}$M.

Antag. of Actin-Myosin-100 μM=80%; 50 μM=67%.

Antag. of MLCP-100 μM=74%; 50 μM=59%.

B.P.-dose 10 mg/kg= −51 mm at 1.5 hours; −54 mm at 4 hours.

EXAMPLE 8

1,4,5,6,7,8-Hexahydro-2-methyl-5-oxo-4(R or S-pentafluorophenyl)-1,7-naphthyridine-3-carboxylic acid (S)-2-methoxy-2-phenylethyl esters Two grams of the product of Example 7 were separated into 2 diastereomers by preparative high performance liquid chromatography on a Waters Prep Pak C18 column using methanol and ammonium phosphate buffer. Diastereomer A (494 mgs) was obtained as the hydrochloride, three quarter hydrate, $[\alpha]_D^{25.4}= +66.70°$ [1.00; MeOH]; Isomeric purity by HPLC, 85.4% diastereomer A and 14.6% diastereomer B.

Analysis for: $C_{25}H_{21}N_2F_5O_4 \cdot HCl \cdot \frac{3}{4}H_2O$. Calculated: C, 53.77; H, 4.24; N, 5.03; Cl, 6.35. Found: C, 53.77; H, 3.98; N, 5.03; Cl, 6.23.

P.R.=50 (Note: Muscles were pre-treated.)

Antag. of Actin-Myosin-100 μM=69%; 50 μM=28%.

Antag. of MLCP-100 μM=63%; 50 μM=28%.

B.P.-dose 50 mg/kg= −73 mm at 1.5 hours; −86 mm at 4 hours.

Diastereomer B (655 mgs) was isolated as the hydrochloride, hemihydrate, $[\alpha]_D^{25.4}= -5.69°$ [1.045; MeOH]; Isomeric purity by HPLC, 88.7% diastereomer B and 11.3% diastereomer A.

Analysis for: $C_{25}H_{21}N_2F_5O_4 \cdot HCl \cdot \frac{1}{2}H_2O$. Calculated: C, 54.20; H, 4.19; N, 5.06; Cl, 6.40. Found: C, 554.08; H, 3.99; N, 5.06; Cl, 6.02.

P.R.=53 (Note: Muscles were pre-treated.)

Antag. of Actin-Myosin-100 μM=64%; 50 μM=30%.

Antag. of MLCP=100 μM=62%; 50 μM=34%.

B.P.-dose 50 mg/kg= −28 mm at 1.5 hours; −67 mm at 4 hours.

EXAMPLE 9

4-(2-Chloro-6-fluorophenyl)-1,4,5,6,7,8-hexahydro-2-methyl-5-oxo-1,7-naphthyridine-3-carboxylic acid 2-methoxy-2-phenylethyl ester A mixture of 15.2 g of 1-benzyl-3-hydroxy-5-oxo-2,3,4,6-tetrahydropyridine hydrate, 17.7 g of 2-methoxy-2-phenylethyl acetoacetate, 11.9 g of 2-chloro-6-fluorobenzaldehyde, 11.5 g of ammonium acetate and 300 ml of methanol was refluxed for 6 hours. The sovlent was removed in vacuo. The residue was dissolved in methylenechloride, washed with water, then dried over magnesium sulfate. The solvent was evaporated in vacuo and the residue was crystallized by trituration with ethyl acetate to obtain 13.7 g of solid, mp. 160°–4° C. Conversion to the hydrochloride afforded 13.6 g of 4-(2-chloro-6-fluorophenyl)-1,4,5,6,7,8-hexahydro-2-methyl-5-oxo-7-(phenylmethyl)-1,7-naphthyridine-3-carboxylic acid 2-methoxy-2-phenylethyl ester hydrochloride, m.p. 191°–4° C.

Analysis for: $C_{32}H_{30}N_2ClFO_4 \cdot HCl$. Calculated: C, 64.32; H, 5.23; N, 4.69; Cl, 11.87. Found: C, 64.17; H, 5.20; N, 4.94; Cl, 11.58.

A mixture of the above solid (11.6 g), 2 ml of concentrated hydrochloric acid, 10 ml of water, 200 ml of methanol and 0.5 g of 10% palladium on carbon were shaken with hydrogen (40 psig initial pressure) for 3 hours. The catalyst was separated and the solution was evaporated to dryness. The residue was dissolved in ethyl acetate and left at room temperature for 3 days. The precipitate was separated and dissolved in 450 ml of refluxing ethanol. The solution was evaporaed to one-third volume and diluted with an equal volume of diethyl ether. After standing overnight, the solid was separated and dried to obtain 6.6 g of the title compound as the hydochloride, mp. 224° C. dec.

Analysis for: $C_{25}H_{24}N_2ClFO_4 \cdot HCl$. Calculated: C, 59.18; H, 4.97; N, 5.52; Cl, 13.98. Found: C, 59.21; H, 4.94; N, 5.54; Cl, 13.69.

P.R.=28.

Antag. of Actin-Myosin-100 μM=40%.

Antag. of MLCP-100 μM=44%.

B.P.-dose 50 mg/kg= −37 mm at 1.5 hours; −14 mm at 4 hours.

EXAMPLE 10

4-(3-chloro-2-methylphenyl)-1,4,5,6,7,8-hexahydro-2-methyl-5-oxo-1,7-naphthyridine-3-carboxylic acid 2-methoxy-2-phenylethyl ester Methanol (200 ml), 15.2 g of 1-benzyl-3-hydroxy-5-oxo-2,3,4,6-tetrahydropyridine hydrate, 17.7 g of 2-methoxy-2-phenylethyl acetoacetate, 11.6 g of 3-chloro-2-methylbenzaldehyde and 11.5 g of ammonium acetate were combined and refluxed for 6 hours. The methanol was evaporated and the residue was dissolved in methylenechloride. The solution was extracted with water, dried over magnesium sulfate, then evaporated to dryness. The viscous residue was dissolved in ethyl acetate and allowed to stand at room temperature for 3 days. The mixture was filtered to obtain 4.5 g of solid, mp. 180°-2° C. Conversion to the hydrochloride afforded 4.7 g of 4(3-chloro-2-methylphenyl)-1,4,5,6,7,8-hexahydro-2-methyl-5-oxo-7-(phenylmethyl)-1,7-naphthyridine-3-carboxylic acid 2-methoxy-2-phenylethyl ester hydrochloride. The hydrochloride was mixed with 200 ml of methanol, 5 ml of concentrated hydrochloric acid, 15 ml of water and 0.5 g of 10% palladium on carbon, then shaken with hydrogen (50 psig initial pressure) for 6 hours. The catalyst was separated and the solutuion was evaporated to dryness in vacuo. The residue was shaken with ethyl acetate and saturated sodium carbonate solution. The ethyl acetate portion was dried over magnesium sulfate, evaporated to a small volume, and left at room temperature for 3 days. The precipitate was separated, suspended in ethyl acetate and treated with hydrogen chloride until solution occurred. Precipitate formed on scratching the sides of the flask. The solid was separated and dried to obtain 2.4 g of the title compound as the hydrochloride, hemihydrate, mp. 160°-3° C.

Analysis for: $C_{26}H_{27}N_2Cl_4.HCl.\frac{1}{2}H_2O$. Calculated: C, 60.94; H, 5.70; N, 5.47; Cl, 13.84. Found: C, 60.93; H, 5.60; N, 5.48; Cl, 14.16.

P.R.=60.

$IC_{25} > 1 \times 10^{-5}M$.

Antag. of Actin-Myosin-100 μM=76±2%; 50 μM=68±2%; 25 μM=45±3%.

Antag. of MLCP-100 μM=75±3%; 50 μM=62±1%; 25 μM=35±5%.

B.P.-dose 10 mg/kg= −28 mm at 1.5 hours; −19 mm at 4 hours.

EXAMPLE 11

4-(3-Chlorophenyl)-1,4,5,6,7,8-hexahydro-2-methyl-5-oxo-1,7 naphthyridine-3-carboxylic acid 2-methoxy-2-phenylethyl ester A mixture of 15.3 g of 1-benzyl-3-hydroxy-5-oxo-2,3,4,6-tetrahydropyridine hydrate, 10.6 g of 3-chlorobenzaldehyde, 17.7 g of 2-methoxy-2-phenylethyl acetoacetate, 12 g of ammonium acetate and 150 ml of methanol was refluxed for 5 huors. The solvent was removed in vacuo. The residue was dissolved in methylenechloride, extracted with water, then dried over magnesium sulfate. The solution was diluted with diethyl ether to the point of cloudiness, then left at room temperature for 18 hours. The supernatant was decanted and the precipitate was slurried with ethanol and filtered to obtain 12.9 g of the solid, mp. 168°-170° C. dec. The solid was suspended in methanol and saturated with hydrogen chloride. The mixture was cooled in an ice bath, then filtered. The solid was recrystallized from ethanol to obtain 11.1 g of 4-(3-chlorophenyl)-1,4,5,6,7,8-hexahydro-2-methyl-5-oxo-7-(phenylmethyl)-1,7-naphthyridine-3-carboxylic acid 2-methoxy-2-phenylethyl ester hydrochloride, mp. 222°-4° C. dec. The hydrochloride (10.8 g), 1 g of 10% palladium on carbon and 450 ml of methanol were shaken with hydrogen at an initial pressure of 48.5 psig. After 4 hours, the catalyst was separated and the solution was evaporated to dryness. The residue was dissolved in methanol, saturated with hydrogen chloride, then evaporated to dryness. The residue was recrystallized from ethanol to obtain 3 g of the title compound as the hydrochloride, monohydrate, mp. 165°-7° C.

Analysis for: $C_{25}H_{25}N_2ClO_4.HCl.H_2O$. Calculated: C, 59.17; H, 5.56; N, 5.52; Cl, 13.97. Found: C, 59.02; H, 5.62; N, 5.70; Cl, 13.51.

P.R.=31.

Antag. of Actin-Myosin-100 μM=53%.

Antag. of MLCP-100 μM=48%.

B.P.-dose 50 mg/kg= −29 mm at 1.5 hours; −38 mm at 4 hours.

EXAMPLE 12

1,4,5,6,7,8-Hexahydro-2-methyl-5-oxo-4-[2-(trifluoromethyl)phenyl]-1,7-naphthyridine-3-carboxylic acid 2-methoxy-2-phenylethyl ester In a manner similar to Example 11, o-trifluoromethylbenzaldehyde, 1-benzyl-3-hydroxy-5-oxo-2,3,4,6-tetrahydropyridine, 2-methoxy-2-phenylethyl acetoacetate and ammonium acetate were reacted to obtain 1,4,5,6,7,8-hexahydro-2-methyl-5-oxo-7-(phenylmlethyl)-4-[2-(trifluoromethyl)phenyl]-1,7-naphthyridine-3-carboxylic acid 2-methoxy-2-phenylethyl ester, isolated as the hydrochloride, m.p. 175°-8° C. dec.

Analysis for: $C_{33}H_{31}N_2F_3O_4.HCl$. Calculated: C, 64.65; H, 5.26; N, 4.57; Cl, 5.78 Found: C, 64.94; H, 5.15; N, 4.47; Cl, 5.95.

Hydrogenation of the above material afforded the title compound as the hydrochloride, m.p. 179°-181° C.

Analysis for: $C_{26}H_{25}N_2F_3O_4.HCl$. Calculated: C, 59.71; H, 5.01; N, 5.36; Cl, 6.78 Found: C, 59.83; H, 5.09; N, 5.54; Cl, 7.18.

P.R.=39.

$IC_{25} = 2 \times 10^{-6}M$.

Antag. of Actin-Myocin-100 μM=30%.

Antag. of MLCP-100 μM=24%.

B.P.-dose 25 mg/kg= −56 mm at 1.5 hours; −56 mm at 4 hours.

EXAMPLE 13

1,4,5,6,7,8-Hexahydro-2-methyl-5-oxo-4-(pentafluorophenyl)-1,7-naphthyridine-3-carboxylic acid 1-methyl-2-phenoxyethyl ester A mixture of 15.2 g of 1-benzyl-3-hydroxy-5-oxo-2,3,4,6-tetrahydropyridine hydrate, 17.7 g of 1-methyl-2-(phenoxy)ethyl acetoacetate, 14.7 g of pentafluorobenzaldehyde, 11.5 g of ammonium acetate and 300 ml of methanol was heated to reflux for 6 hours. After evaporation of the methanol, the solid residue was dissolved in methylenechloride and extracted with water. The methylenechloride solution was dried over magnesium sulfate, then evaporated to dryness. The residue was recrystallized from ethyl acetate-hexane to obtain 14 g of solid, m.p. 204°-8° C. Conversion to the hydrochloride afforded 8.6 g of 1,4,5,6,7,8-hexahydro-2-methyl-5-oxo-4-(pentafluorophenyl)-7-(phenylmethyl)-1,7-naphthyridine-3-carboxylic acid 1-methyl-2-(phenoxy)ethyl ester hydrochloride, m.p. 215°–7° C.

Analysis for: $C_{32}H_{27}N_2F_5O_4 \cdot HCl$. Calculated: C, 60.52; H, 4.44; N, 4.41; Cl, 5.58 Found: C, 60.80; H, 4.47; N, 4.45; Cl, 5.54.

The above hydrochloride (7.6 g), 200 ml of methanol, 5 ml of concentrated hydrochloric acid, 15 ml of water and 0.5 g of 10% palladium on carbon were shaken with hydrogen (50 psig initial pressure) for 6 hours. The catalyst was removed and the solution was evaporated in vacuo. The residue was shaken with diethyl ether and saturated sodium carbonate solution. The ether solution was dried over magnesium sulfate, then evaporated to dryness. The solid residue was suspended in methanol and treated with hydrogen chloride until solution occurred. The solvent was removed in vacuo and the residue was left standing with ethyl acetate-hexane for 3 days. The solid was separated and dried to obtain 3.2 g of the title compound as the hydrochloride, m.p. indefinite.

Analysis for: $C_{25}H_{21}N_2F_5O_4 \cdot HCl$. Calculated: C, 55.10; H, 4.07; N, 5.14; Cl, 6.51. Found: C, 54.62; H, 4.06; N, 5.02; Cl, 6.55.

P.R.=46.

$IC_{25}=1\times10^{-5}M$.

Antag. of Actin-Myosin-100 $\mu M=78\%$; 25 $\mu M=61\%$.

Antag. of MLCP-100 $\mu M=70\%$; 25 $\mu M=58\%$.

B.P.-dose 50 mg/kg= −35 mm at 1.5 hours; −60 mm at 4 hours.

EXAMPLE 14

1,4,5,6,7,8-Hexahydro-2-methyl-5-oxo-4-(pentafluorophenyl)-1,7-naphthyridine-3-carboxylic acid 2,3-dihydro-1,4-benzodioxin-2-ylmethyl ester Methanol (300 ml), 15.2 g of 1-benzyl-3-hydroxy-5-oxo-2,3,4,6-tetrahydropyridine hydrate, 18.8 g of 2,3-dihydro-1,4-benzodioxin-2-ylmethyl acetoacetate, 14.7 g of pentafluorobenzaldehyde, and 11.5 g of ammonium acetate were combined and heated at reflux for 6 hours. The mixture was cooled, then the precipitate was separated by filtration. The solid was dissolved in methylenechloride, extracted with water, then dried over magnesium sulfate and evaporated to dryness. The residue was slurried with diethyl ether and filtered to obtain 14.6 g of solid, m.p. 215°–200° C. dec. Conversion to the hydrochloride afforded 15.2 g of 1,4,5,6,7,8-hexahydro-2-methyl-5-oxo-4-(pentafluorophenyl)-7-(phenylmethyl)-1,7-naphthyridine-3-carboxylic acid (2,3-dihydro-1,4-benzodioxin-2-yl)methyl ester hydrochloride, m.p. 190°–3° C.

Analysis for: $C_{32}H_{25}N_2F_5O_5 \cdot HCl$. Calculated: C, 59.22; H, 4.04; N, 4.31; Cl, 5.46. Found: C, 59.96; H, 4.00; N, 4.27; Cl, 5.52.

Twelve grams of the above hydrochloride, 200 ml of methanol, 5 ml of concentrated hydrochloric acid, 15 ml of water and 0.5 g of 10% palladium on carbon were shaken with hydrogen (50 psig initial pressure) for 6 hours. After separation of the catalyst, the solution was evaporated to dryness to vacuo. The residue was dissolved in ethyl acetate and water. The ethyl acetate portion was dried over magnesium sulfate, then evaporated to dryness. The residue solidified on standing with ethanol-ether for 3 days. The solid was treated with boiling hexane, filtered and dried to obtain 4.2 g of the title compound as the hydrochloride, m.p. 167°–170° C.

Analysis for: $C_{25}H_{19}N_2F_5O_5 \cdot HCl$. Calculated: C, 53.72; H, 3.61; N, 5.01; Cl, 6.34. Found: C, 53.51; H, 3.64; N, 5.00; Cl, 6.09.

P.R.=62.

$IC_{25}=3.2\times10^{-6}M$.

Antag. of Actin-Myosin-100 $\mu M=80\%$; 25 $\mu M=65\%$.

Antag. of MLCP-100 $\mu M=76\%$; 25 $\mu M=59\%$.

B.P.-dose 50 mg/kg= −46 mm at 1.5 hours; −42 mm at 4 hours.

EXAMPLE 15

1,4,5,6,7,8-Hexahydro-2-methyl-4-(2-methylphenyl)-5-oxo-1,7-naphthyridine-3-carboxylic acid 2-phenoxyethyl ester A mixture of 15.2 g of 1-benzyl-3-hydroxy-5-oxo-2,3,4,6-tetrahydropyridine hydrate, 16.6 g of 2-phenoxyethyl acetoacetate, 9 g of o-tolualdehyde, 11.5 g of ammonium acetate and 300 ml of methanol was refluxed 6 hours. The solvent was evaporated to the point of crystallization, then cooled and filtered to obtain 22.7 g of solid, m.p. 165°–7° C. The solid was dissolved in methanol and saturated with hydrogen chloride. The precipitated solid was separated, washed with methanol and dried to obtain 23.5 of 1,4,5,6,7,8-hexahydro-2-methyl-4-(2-methylphenyl)-5-oxo-7-(phenylmethyl)-1,7-naphthyridine-3-carboxylic acid 2-phenoxyethyl ester hydrochloride, m.p. 219°–222° C.

Analysis for: $C_{32}H_{32}N_2O_4 \cdot HCl$. Calculated: C, 60.51; H, 6.10; N, 5.14; Cl, 6.50. Found: C, 70.49; H, 5.96; N, 5.03; Cl, 6.20.

The hydrochloride from above (21.5 g), 500 ml of methanol, 5 ml of concentrated hydrochloric acid, 15 ml of water and 0.6 g of 10% palladium on carbon were shaken with hydrogen (50 psig initial pressure) for 20 hours. The catalyst was separated and the solution was evaporated to dryness in vacuo. The residue was slurried with diethyl ether and filtered. The solid was triturated with refluxing ethanol, filtered and dried to obtain 12 g of the title compound as the hydrochloride, m.p. 238°–240° C. dec.

Analyais for: $C_{25}H_{26}N_2O_4 \cdot HCl$. Calculated: C, 66.00; H, 5.98; N, 6.16; Cl, 7.79. Found: C, 66.28; H, 5.91; N, 6.31; Cl, 8.09.

P.R.=63.

$IC_{25}=4.7\times10^{-6}M$.

Antag. of Actin-Myosin-100 $\mu M=66\pm5\%$.

Antag. of MLCP-100 $\mu M=61\pm5\%$.

B.P.-dose 25 mg/kg= −29 mm at 1.5 hours; −39 mm at 4 hours.

EXAMPLE 16

1,4,5,6,7,8-Hexahydro-2-methyl-5-oxo-4-(2,3,6-trifluorophenyl)-1,7-naphthyrdine-3-carboxylic acid 2-phenoxyethyl ester Eight grams of 2,3,6-trifluorobenzaldehyde, 10.2 g of 1-benzyl-3-hydroxy-5-oxo-2,3,4,6-tetrahydropyridine hydrate, 11.5 g of 2-phenoxyethyl acetoacetate, 7.7 g of ammonium acetate and 125 ml of methanol were combined and refluxed 6 hours. The mixture was evaporated to dryness in vacuo. The residue was dissolved in methylenechloride and extracted with water. The methylenechloride solution was evaporated and the residue was dissolved in ethanol and re-evaporated. The residue was triturated with ethanol until it solidified.

The mixture was filtered to obtain 12 g of solid, m.p. 168°–9° C. The solid was suspended in methanol and treated with hydrogen chloride. The solution was evaporated and the residue was triturated with diethyl ether to obtain 12.5 g of 1,4,5,6,7,8-hexahydro-2-methyl-5-oxo-7-(phenylmethyl)-4-(2,3,6-trifluorophenyl)-1,7-naphthyridine-3-carboxylic acid 2-phenoxyethylester hydrochloride.

The above solid, 200 ml of methanol, 10 ml of water, 5 ml of concentrated hydrochloric acid and 1 g of 10% palladium on carbon were shaken with hydrogen at an intial pressure of 50 psig. After 5 hours, the catalyst was separated and the solution was evaporated to dryness. The residue was slurried with ethanol and filtered. The solid was recrystallized from methanol-diethyl ether to obtain 7 g of the title compound as the hydrochloride, m.p. 252°–5° C. dec.

Analysis for: $C_{24}H_{21}N_2F_3O_4.HCl$. Calculated: C, 58.24; H, 4.48; N, 5.66; Cl, 7.17. Found: C, 58.22; H, 4.34; N, 5.68; Cl, 7.27.

P.R.=63.

Antag. of Actin-Myosin-100 $\mu M=34\%$.

Antag. of MLCP-100 $\mu M=28\%$.

B.P.-dose 25 mg/kg= −37 mm at 1.5 hours; −18 mm at 4 hours.

EXAMPLE 17

4-(3-Chloro-2-methylphenyl)-1,4,5,6,7,8-hexahydro-2-methyl-5-oxo-1,7-naphthyridine-3-carboxylic acid 2-phenoxyethyl ester A mixture of 14.2 g of 1-benzyl-3-hydroxy-5-oxo-2,3,4,6-tetrahydropyridine hydrate, 10.8 g of 3-chloro-2-methylbenzaldehyde, 15.6 g of 2-phenoxyethyl acetoacetate, 10.8 g of ammonium acetate and 300 ml of methanol was heated at reflux for 6 hours. The solvent was evaporated and the residue was dissolved in methylenechloride. The methylenechloride solution was extracted with water, dried over magnesium sulfate, then evaporated to dryness. The residue was crystallized from ethanol to obtain 6.4 g of solid, m.p. 188°–190° C. The solid was suspended in methanol and treated with hydrogen chloride to obtain 6.3 g of 4-(3-chloro-2-methylphenyl)-1,4,5,6,7,8-hexahydro-2-methyl-5-oxo-7-(phenylmethyl)-1,7-naphthyridine-3-carboxylic acid 2-phenoxyethyl ester hydrochloride, m.p. 202°–5° C.

The solid from above, 200 ml of ethanol, 5 ml of concentrated hydrochloric acid, 15 ml of water and 0.5 g of 10% palladium on carbon were shaken with hydrogen at an initial pressure of 50 psig. After 3 hours, the catalyst was separated and the solution was evaporated to dryness. The residue was dissolved in ethanol and evaporated to dryness (3 times). The solid was recrystallized from ethanol to obtain 1.7 g of the title compound as the hydrochloride, m.p. 233°–5° C.

Analysis for: $C_{26}H_{25}N_2ClO_4.HCl$. Calculated: C, 61.35; H, 5.35; N, 5.72; Cl, 14.48. Found: C, 61.17; H, 5.31; N, 5.69; Cl, 14.14.

P.R.=74.

$IC_{25}=1\times 10^{-6}M$.

Antag. of Actin-Myosin-100 $\mu M=71\pm 2\%$; 50 $\mu M=64\pm 3\%$; 25 $\mu M=44\pm 2\%$; 10 $\mu M=22\%$.

Antag. of MLCP-100 $\mu M=67\pm 2\%$; 50 $\mu M=59\pm 3\%$; 25 $\mu M=39\pm 2\%$; 10 $\mu M=11\%$.

B.P.-dose 25 mg/kg= −10 mm at 1.5 hours; −45 mm at 4 hours.

EXAMPLE 18

1,4,5,6,7,8-Hexahydro-2-methyl-5-oxo-4-(pentafluorophenyl)-1,7-naphthyridine-3-carboxylic acid 2-phenylethyl ester A mixture of 12 g of 1-benzyl-3-hydroxy-5-oxo-2,3,4,6-tetrahydropyridine, 11.8 g of pentafluorobenzaldehyde, 12.6 g of phenylethyl acetoacetate, 14 g of ammonium acetate and 200 ml of isopropanol was refluxed for 5 hours. The solution was evaporated to dryness in vacuo. The residue was slurried with 95% ethanol and filtered. The solid was washed with water and methanol, then dried to obtain 15.3 g of material, m.p. 213°–5° C. The solid was suspended in methanol and saturated with hydrogen chloride. The solution was evaporated to dryness. The residue was dissolved in ethanol and re-evaporated. The residue was slurried with 50:50 ethanol/diethyl ether and filtered to obtain 11.8 g of 1,4,5,6,7,8-hexahydro-2-methyl-5-oxo-7-(phenylmethyl)-4-(pentafluorophenyl)-1,7-naphthyridine-3-carboxylic acid 2-phenylethyl ester hydrochloride, m.p. 213° C. The hydrochloride, 450 ml of methanol and 1 g of 10% palladium on carbon were shaken with hydrogen (47.5 psig initial pressure) for 3.5 hours. The catalyst was separated and the solution was evaporated to dryness in vacuo. The residue was dissolved in methylenechloride, dried over magnesium sulfate, then evaporated to dryness in vacuo. The solid residue was re-precipitated from methylenechloride-hexane to obtain the title compound as the hydrochloride, hemihydrate, m.p. indefinite.

Analysis for: $C_{24}H_{19}N_2F_5O_3.HCl.\frac{1}{2}H_2O$. Calculated: C, 55.02; H, 4.04; N, 5.35; Cl, 6.77. Found: C, 55.19; H, 3.91; N, 5.43; Cl, 7.11.

P.R.=48.

$IC_{25}=1\times 10^{-6}M$.

Antag. of Actin-Myosin-100 $\mu M=78\pm 2\%$; 50 $\mu M=65\%$; 25 $\mu M=42\%$.

Antag. of MLCP-100 $\mu M=77\pm 3\%$; 50 $\mu M=64\%$; 25 $\mu M=35\%$.

B.P.-dose 10 mg/kg= −27 mm at 1.5 hours; −24 mm at 4 hours.

EXAMPLE 19

4-(2,3-Dichlorophenyl)-1,4,5,6,7,8-hexahydro-2-methyl-5-oxo-1,7-naphthyridine-3-carboxylic acid 2-phenoxyethyl ester, hydrochloride Methanol (300 ml), 16.6 g of 1-benzyl-3-hydroxy-5-oxo-2,3,4,6-tetrahydropyridine hydrate, 13.2 g of 2,3-dichlorobenzaldehyde, 16.7 g of 2-phenoxyethyl acetoacetate, and 11.6 g of ammonium acetate were combined and refluxed for 6 hours. The mixture was cooled and filtered to obtain 8.3 g of solid, m.p. 186°–8° C. dec. Conversion to the hydrochloride afforded 8.2 g of 4-(2,3-dichlorophenyl)-1,4,5,6,7,8-hexahydro-2-methyl-5-oxo-7-phenylmethyl-1,7-naphthyridine-3-carboxylic acid 2-phenoxyethyl ester hydrochloride, m.p. 208°–210° C. dec. The solid, 400 ml of methanol, 3 ml of concentrated hydrochloric acid and 0.5 g of 10% palladium on carbon were shaken with hydrogen (48.5 psig initial pressure) for 18 hours. The catalyst was separated and the solution was evaporated to dryness. The residue was recrystallized three times from methanol to obtain the title compound as the hydrochloride, m.p. 228°–230° C. dec.

Analysis for: $C_{24}H_{22}N_2Cl_2O_4 \cdot HCl$. Calculated: C, 56.53; H, 4.55; N, 5.50; Cl, 20.86. Found: C, 56.39; H, 4.75; N, 5.52; Cl, 20.56.

P.R.=62.

$IC_{25}=2.5\times 10^{-6}M$.

Antag. of Actin-Myosin-100 $\mu M=71\%$.

Antag. of MLCP-100 $\mu M=69\%$.

B.P.-dose 50 mg/kg = −50 mm at 1.5 hours; −73 mm at 4 hours.

EXAMPLE 20

1,4,5,6,7,8-Hexahydro-2-methyl-5-oxo-4-(pentafluorophenyl)-1,7-naphthyridine-3-carboxylic acid 2-methyl-2-phenoxypropyl ester, hydrochloride A mixture of 11.8 g of 1-benzyl-3-hydroxy-5-oxo-2,3,4,6-tetrahydropyridine hydrate, 13.3 g of (2-methyl-2-phenoxy)propyl acetoacetate, 10.6 g of pentafluorobenzaldehyde, 8.5 g of ammonium acetate and 125 ml of methanol were combined and refluxed for 4 hours. The mixture was cooled, diluted with 125 ml of 95% ethanol, then filtered to obtain 17 g of solid, m.p. 190°-3° C. The solid was suspended in methanol and treated with hydrogen chloride to afford 17 g of 1,4,5,6,7,8-hexahydro-2-methyl-5-oxo-4-(pentafluorophenyl)-7-phenylmethyl-1,7-naphthyridine-3-carboxylic acid 2-methyl-2-phenoxypropyl ester hydrochloride, m.p. 176°-9° C.

The above hydrochloride (15 g), 400 ml of methanol, 10 ml of water, 8 ml of concentrated hydrochloric acid, and 1 g of 10% palladium on carbon were shaken with hydrogen (50 psig initial pressure) for 4.5 hours. The catalyst was separated and the filtrate was evaporated to dryness in vacuo. The residue was dissolved in methylene chloride and shaken with saturated sodium carbonate solution. The methylene chloride solution was separated and a precipitate formed after 20 minutes. The mixture was filtered to obtain 6.5 g of solid, m.p. 170°-3° C. The solid was dissolved in methanol and treated with hydrogen chloride to obtain 4.9 g of the title compound as the hydrochloride.

Analysis for: $C_{26}H_{23}F_5N_2O_4 \cdot HCl$. Calculated: C, 55.89; H, 5.01; N, 5.01; Cl, 6.34. Found: C, 55.48; H, 4.31; N, 5.03; Cl, 6.70.

P.R.=51.

Antag. of Actin-Myosin-100 $\mu M=67\%$.

Antag. of MLCP-100 $\mu M=62\%$.

B.P.-dose 25 mg/kg = −64 mm at 1.5 hours; −41 mm at 4 hours.

EXAMPLE 21

1,4,5,6,7,8-Hexahydro-2-methyl-5-oxo-4-(pentafluorophenyl)-1,7-naphthyridine-3-carboxylic acid 4-phenoxybutyl ester Pentafluorobenzaldehyde (12.5 g), 15.6 g of 4-phenoxybutyl acetoacetate, 15 g of 1-benzyl-3-hydroxy-5-oxo-2,3,4,6-tetrahydropyridine hydrate, 11 g of ammonium acetate and 200 ml of methanol were combined and heated to reflux. A precipitate formed after one-half hour. After heating for 5.5 hours, the mixture was cooled and filtered to obtain 9.5 g of 1,4,5,6,7,8-hexahydro-2-methyl-5-oxo-4-(pentafluoro)-7-(phenylmethyl)-1,7-naphthyridine-3-carboxylic acid 4-phenoxybutyl ester, m.p. 229°-231° C. The solid was dissolved in 200 ml of methanol and saturated with hydrogen chlorode. Water (10 ml) and 0.6 g of 10% palladium on carbon were added and the mixture was shaken with hydrogen (50 psig initial pressure) for 5 hours. The catalyst was separated and the solution was concentrated to dryness. The residue was dissolved in ethanol and evaporated to dryness. This was repeated until a solid residue was obtained. The residue was recrystallized from ethanol to obtain 4.8 g of the title compound as the hydrochloride, m.p. 210° C. dec.

Analysis for: $C_{26}H_{23}N_2F_5O_4 \cdot HCl$. Calculated: C, 55.87; H, 4.33; N, 5.01; Cl, 6.34. Found: C, 55.74; H, 4.23; N, 4.99; Cl, 6.59.

P.R.=61.

$IC_{25}=1\times 10^{-6}M$.

Antag. of Actin-Myosin-100 $\mu M=80\%$.

Antag. of MLCP-100 $\mu M=77\%$.

B.P.-dose 25 mg/kg=0 mm at 1.5 hours; −49 mm at 4 hours.

EXAMPLE 22

1,4,5,6,7,8-Hexahydro-2-methyl-5-oxo-4-(pentafluorophenyl)-1,7-naphthyridine-3-carboxylic acid 2-(2,3-dichlorophenoxy)ethyl ester Methanol (250 ml), 9.1 g of 1-benzyl-3-hydroxy-5-oxo-2,3,4,6-tetrahydropyridine hydrate, 13.3 g of 2-(2,3-dichlorophenoxy)ethyl acetoacetate, 8.8 g of pentafluorobenzaldehyde, and 6.9 g of ammonium acetate were combined and refluxed for 6 hours. The mixture was cooled and filtered. The solid was dissolved in ethyl acetate, extracted with water, then dried over magnesium sulfate. Evaporation of the solvent afforded 12 g of solid, m.p. 223°-6° C. dec. The solid in methanol was treated with hydrogen chloride to obtain 12.4 g of 1,4,5,6,7,8-hexahydro-2-methyl-5-oxo-7-(phenylmethyl)-4-(pentafluorophenyl)-1,7-naphthyridine-3-carboxylic acid 2-(2,3-dichlorophenoxy)ethyl ester hydrochloride, m.p. 223°-6° C. dec.

The hydrochloride from above (10 g), 500 ml of methanol, 25 ml of water, 5 ml of concentrated hydrochloric acid and 0.5 g of 10% palladium on carbon were shaken with hydrogen (45 psig initial pressure) for 4 hours. The catalyst was separated and the solution was evaporated to dryness. The residue was dissolved in ethyl acetate and shaken with dilute sodium hydroxide solution. The ethyl acetate solution was dried over magnesium sulfate, then evaporated to dryness. The residue was dissolved in methanol and saturated with hydrogen chloride. The solution was evaporated to dryness. The residue crystallized on standing with ethyl acetate for 3 days. The solid was treated with boiling ethyl acetate and filtered to obtain the title compound as the hydrochloride, m.p. 228°-231° C. dec.

Analysis for: $C_{24}H_{17}N_2Cl_2F_5O_4 \cdot HCl$. Calculated: C, 48.06; H, 3.02; N, 4.67; Cl, 17.74. Found: C, 48.38; H, 3.04; N, 4.71; Cl, 17.40.

P.R.=61.

$IC_{25}=1\times 10^{-6}M$.

Antag. of Actin-Myosin-100 $\mu M=78\pm 1\%$; 50 $\mu M=75\pm 4\%$; 25 $\mu M=54\pm 3\%$; 10 $\mu M=30\pm 3\%$.

Antag. of MLCP-100 $\mu M=74\pm 2\%$; 50 $\mu M=73\pm 1.5\%$; 25 $\mu M=54\pm 2.5\%$; 10 $\mu M=25\%$.

B.P.-dose 25 mg/kg = −37 mm at 1.5 hours; −52 mm at 4 hours.

EXAMPLE 23

4-(2-chloro-6-fluoro-3-methylphenyl)-1,4,5,6,7,8-hexahydro-2-methyl-5-oxo-1,7-naphthyridine-3-carboxylic acid 2-phenoxyethyl ester Methanol (200 ml), 16.6 g of 1-benzyl-3-hydroxy-5-oxo-2,3,4,6-tetrahydropyridine hydrate, 16.6 g of 2- phenoxyethyl acetoacetate, 13 g of 2-chloro-6-fluoro-3-methylbenzaldehyde and 10 g of ammonium acetate were combined and refluxed for 5 hours. The solution was evaporated to dryness. The residue was dissolved in methylenechloride, extracted with water, then dried over magnesium sulfate. The solvent was evaporated and the residue was left standing with diethyl ether for 18 hours. The ether was decanted from the solid residue. The residue was treated with hot methanol and filtered to obtain 22 g of solid, m.p. 174°-7° C. The solid was suspended in methanol and treated with hydrogen chloride. The solution was evaporated and the residue was dissolved in 100 ml of methanol. After 2 days at room temperature, the solid was separated and recrystallized from ethanol to obtain 13.5 g of 4-(2-chloro-6-fluoro-3-methylphenyl)-1,4,5,6,7,8-hexahydro-2-methyl-5-oxo-7-(phenylmethyl)-1,7-naphthyridine-3-carboxylic acid 2-phenoxyethyl ester hydrochloride, m.p. 185°-7° C.

Twelve grams of the above hydrochloride, 125 ml of methanol, 2 ml of concentrated hydrochloric acid, 10 ml of water, and 1 g of 10% palladium on carbon were shaken with hydrogen (50 psig initial pressure) for 24 hours. The mixture was diluted with 500 ml of methanol, heated to reflux and filtered. The filtrate was evaporated to dryness and the residue was slurried with ethanol and filtered. The solid was recrystallized from methanol to obtain 5.2 g of the title compound as the hydrochloride, m.p. 252°-5° C. dec.

Analysis for: $C_{25}H_{24}N_2ClFO_4.HCl$. Calculated: C, 59.18; H, 4.97; N, 5.52; Cl, 13.98. Found: C, 59.12; H, 4.91; N, 5.56; Cl, 14.50.

P.R.=67.

Antag. of Actin-Myosin-100 $\mu M=62\%$; 50 $\mu M=23\%$.

Antag. of MLCP-100 $\mu M=56\%$; 50 $\mu M=18\%$.

B.P.-dose 25 mg/kg = −22 mm at 1.5 hours; −31 mm at 4 hours.

EXAMPLE 24

4-(2,3-Dichloro-6-fluorophenyl)-1,4,5,6,7,8-hexahydro-2-methyl-5-oxo-1,7-naphthyridine-3-carboxylic acid 2-phenoxyethyl ester 2,3-Dichloro-6-fluorobenzaldehyde was prepared by a method analogous to the preparation of 2,3-difluorobenzaldehyde (Roe, A. M., et a., J. Med. Chem., 11, 814, 1968).

Fifty-nine grams of 3,4-dichlorofluorobenzene were converted to 59.7 g of 2,3-dichloro-6-fluorobenzaldehyde, m.p. 55°-7° C.

Analysis for: $C_7H_3Cl_2FO$. Calculated: C, 43.56; H, 1.56; Cl, 36.74. Found: C, 43.17; H, 1.69; Cl, 36.96.

A mixture of 15.2 g of 1-benzyl-3-hydroxy-5-oxo-2,3,4,6-tetrahydropyridine hydrate, 16.6 g of 2-phenoxyethyl acetoacetate, 14.4 g of 2,3-dichloro-6-fluorobenzaldehyde, 11.5 g of ammonium acetate and 300 ml of methanol was refluxed for 6 hours. The solution was evaporated to dryness. The residue was dissolved in methylenechloride, extracted with water, then dried over magnesium sulfate. The solution was evaporated and the residue was crystallized from ethyl acetate. The mixture was filtered to obtain 16.4 g of solid, m.p. 178°-180° C. Treatment with hydrogen chloride in methanol afforded 14.3 g of 4-(2,3-dichloro-6-fluorophenyl)-1,4,5,6,7,8-hexahydro-2-methyl-5-oxo-7-(phenylmethyl)-1,7-naphthyridine-3-carboxylic acid 2-phenoxyethyl ester hydrochloride, m.p. 185° C. dec.

The above hydrochloride (11.2 g), 500 ml of methanol, 25 ml of water, 5 ml of concentrated hydrochloric acid, and 0.5 g of 10% palladium on carbon were shaken with hydrogen (45 psig initial pressure) for 4 hours. The catalyst was separated and the solution was evaporated to dryness in vacuo. The residue was recrystallized from methanol-diethyl ether to obtain 7.8 g of the title compound as the hydrochloride, m.p. 235°-6° C. dec.

Analysis for: $C_{24}H_{21}N_2Cl_2FO_4.HCl$. Calculated: C, 54.61; H, 4.20; N, 5.31; Cl, 20.15. Found: C, 54.90; H, 4.18; N, 5.35; Cl, 20.27.

P.R.=65.

$IC_{25}=1\times10^{-5}M$.

Antag. of Actin-Myosin-100 $\mu M=72\pm1\%$; 50 $\mu M=54\pm3\%$; 25 $\mu M=9\pm2\%$.

Antag. of MLCP-100 $\mu M=68\pm1\%$; 50 $\mu M=50\pm2\%$; 25 $\mu M=8\pm2\%$.

B.P.-dose 25 mg/kg= −50 mm at 1.5 hours; −70 mm at 4 hours;

10 mg/kg= −6 mm at 1.5 hours; −26 mm at 4 hours;

5 mg/kg= −17 mm at 1.5 hours; −26 mm at 4 hours.

What is claimed is:

1. A compound of the formula:

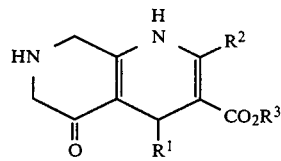

in which $R^1$ is tetra- or penta-chloro, bromo or fluoro-phenyl or

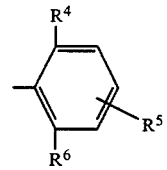

where $R^4$ and $R^6$ are, independently, hydrogen, alkyl of 1 to 6 carbon atoms, halo, trifluoromethyl, alkoxy of 1 to 6 carbon atoms, alkylthio of 1 to 6 carbon atoms, cyano or nitro; and $R^5$ is hydrogen, alkyl of 1 to 6 carbon atoms, halo, trifluoromethyl, cyano or nitro;

$R^2$ is alkyl of 1 to 6 carbon atoms; and $R^3$ is

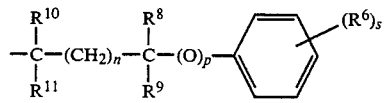

where $R^6$ is, independently, hydrogen, —Cl, —Br, —F, and no more than three of the groups —$CF_3$, alkyl of 1 to 6 carbon atoms or alkoxy of 1 to 6 carbon atoms;

$R^8$ is hydrogen, alkyl of 1 to 6 carbon atoms or alkoxy of 1 to 6 carbon atoms;

$R^9$, $R^{10}$ and $R^{11}$ are, independently, hydrogen or alkyl of 1 to 6 carbon atoms;

n is one of the integers 0, 1, 2, 3 or 4;

s is one of the integers 1, 2, 3, 4 or 5;

p is one of the integers 0 or 1, with the proviso that when $R^8$ is alkoxy, p is 0;

or $R^3$ is

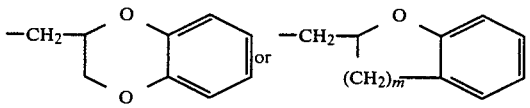

where m is one of the integers 1, 2, 3 or 4;

or a pharmaceutically acceptable salt thereof.

2. A compound of claim 1 of the formula:

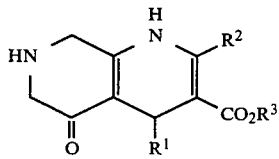

in which $R^1$ is tetra- or penta-chloro, bromo or fluoro-phenyl or

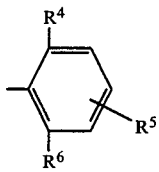

where $R^4$ and $R^6$ are halo; and $R^5$ is hydrogen, alkyl of 1 to 6 carbon atoms, halo, trifluoromethyl, cyano or nitro;

$R^2$ is alkyl of 1 to 6 carbon atoms; and $R^3$ is

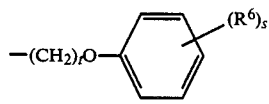

where t is one of the integers 2, 3, 4, 5, or 6;

$R^6$ is, independently, hydrogen, —Cl, —Br, —F, and no more than three of the groups —$CF_3$, alkyl of 1 to 6 carbon atoms or alkoxy of 1 to 6 carbon atoms; and s is one of the integers 1, 2, 3, 4 or 5;

or a pharmaceutically acceptable salt thereof.

3. A compound of claim 1 of the formula:

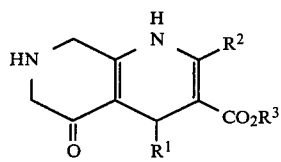

in which $R^1$ and $R^2$ are as defined in claim 1, and $R^3$ is

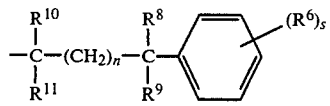

where n, s, $R^6$, $R^9$, $R^{10}$ and $R^{11}$ are as defined in claim 1, and $R^8$ is alkoxy of 1 to 6 carbon atoms; or a pharmaceutically acceptable salt thereof.

4. A compound of claim 1 of the formula:

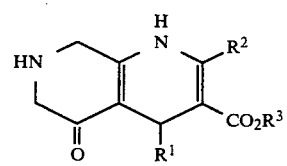

in which $R^1$ and $R^2$ are as defined in claim 1, and $R^3$ is

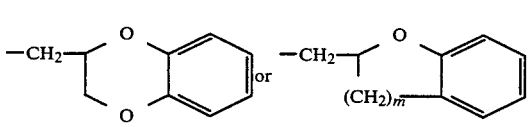

where m is one of the integers 1, 2, 3 or 4; or a pharmaceutically acceptable salt thereof.

5. The compound of claim 1 which is 4-(2,3-dichlorophenyl)-1,4,5,6,7,8-hexahydro-2-methyl-5-oxo-1,7-naphthyridine-3-carboxylic acid 2-methoxy-2-phenylethyl ester or a pharmaceutically acceptable salt thereof.

6. The compound of claim 1 which is 1,4,5,6,7,8-hexahydro-2-methyl-5-oxo-4-(pentafluorophenyl)-1,7-naphthyridine-3-carboxylic acid 2-phenoxyethyl ester or a pharmaceutically acceptable salt thereof.

7. The compound of claim 1 which is (—)-1,4,5,6,7,8-hexahydro-2-methyl-5-oxo-4-(pentafluorophenyl)-1,7-naphthyridine-3-carboxylic acid 2-phenoxyethyl ester or a pharmaceutically acceptable salt thereof.

8. The compound of claim 1 which is (+)-1,4,5,6,7,8-hexahydro-2-methyl-5-oxo-4-(pentafluorophenyl)-1,7-naphthyridine-3-carboxylic acid 2-phenoxyethyl ester or a pharmaceutically acceptable salt thereof.

9. The compound of claim 1 which is 1,4,5,6,7,8-hexahydro-2-methyl-5-oxo-4-(pentafluorophenyl)-1,7-naphthyridine-3-carboxylic acid 2-methoxy-2-phenylethyl ester or a pharmaceutically acceptable salt thereof.

10. The compound of claim 1 which is 1,4,5,6,7,8-hexahydro-2-methyl-5-oxo-4-(pentafluorophenyl)-1,7-naphthyridine-3-carboxylic acid (R)-2-methoxy-2-phenylethyl ester or a pharmaceutically acceptable salt thereof.

11. The compound of claim 1 which is 1,4,5,6,7,8-hexahydro-2-methyl-5-oxo-4-(pentafluorophenyl)-1,7-naphthyridine-3-carboxylic acid (S)-2-methoxy-2-phenylethyl ester or a pharmaceutically acceptable salt thereof.

12. The compound of claim 1 which is 1,4,5,6,7,8-hexahydro-2-methyl-5-oxo-4R-(pentafluorophenyl)-1,7-naphthyridine-3-carboxylic acid (S)-2-methoxy-2- phenylethyl ester or a pharmaceutically acceptable salt thereof.

13. The compound of claim 1 which is 1,4,5,6,7,8-hexahydro-2-methyl-5-oxo-4S-(pentafluorophenyl)-1,7-naphthyridine-3-carboxylic acid (S)-2-methoxy-2-phenylethyl ester or a pharmaceutically acceptable salt thereof.

14. The compound of claim 1 which is 4-(2-chloro-6-fluorophenyl)-1,4,5,6,7,8-hexahydro-2-methyl-5-oxo-1,7-naphthyridine-3-carboxylic acid 2-methoxy-2-phenylethyl ester or a pharmaceutically acceptable salt thereof.

15. The compound of claim 1 which is 4-(3-chloro-2-methylphenyl)-1,4,5,6,7,8-hexahydro-2-methyl-5-oxo-1,7-naphthyridine-3-carboxylic acid 2-methoxy-2-phenylethyl ester or a pharmaceutically acceptable salt thereof.

16. The compound of claim 1 which is 4-(3-chlorophenyl)-1,4,5,6,7,8-hexahydro-2-methyl-5-oxo-1,7-naphthyridine-3-carboxylic acid 2-methoxy-2-phenylethyl ester or a pharmaceutically acceptable salt thereof.

17. The compound of claim 1 which is 1,4,5,6,7,8-hexahydro-2-methyl-5-oxo-4-[2-(trifluoromethyl)phenyl]-1,7-naphthyridine-3-carboxylic acid 2-methoxy-2-phenylethyl ester or a pharmaceutically acceptable salt thereof.

18. The compound of claim 1 which is 1,4,5,6,7,8-hexahydro-2-methyl-5-oxo-4-(pentafluorophenyl)-1,7-naphthyridine-3-carboxylic acid 1-methyl-2-phenoxyethyl ester or a pharmaceutically acceptable salt thereof.

19. The compound of claim 1 which is 1,4,5,6,7,8-hexahydro-2-methyl-5-oxo-4-(pentafluorophenyl)-1,7-naphthyridine-3-carboxylic acid 2,3-dihydro-1,4-benzodioxin-2-ylmethyl ester or a pharmaceutically acceptable salt thereof.

20. The compound of claim 1 which is 1,4,5,6,7,8-hexahydro-2-methyl-4-(2-methylphenyl)-5-oxo-1,7-naphthyridine-3-carboxylic acid 2-phenoxyethyl ester or a pharmaceutically acceptable salt thereof.

21. The compound of claim 1 which is 1,4,5,6,7,8-hexahydro-2-methyl-5-oxo-4-(2,3,6-trifluorophenyl)-1,7-naphthyrdine-3-carboxylic acid 2-phenoxyethyl ester or a pharmaceutically acceptable salt thereof.

22. The compound of claim 1 which is 4-(3-chloro-2-methylphenyl)-1,4,5,6,7,8-hexahydro-2-methyl-5-oxo-1,7-naphthyridine-3-carboxylic acid 2-phenoxyethyl ester or a pharmaceutically acceptable salt thereof.

23. The compound of claim 1 which is 1,4,5,6,7,8-hexahydro-2-methyl-5-oxo-4-(pentafluorophenyl)-1,7-naphthyridine-3-carboxylic acid 2-phenylethyl ester or a pharmaceutically acceptable salt thereof.

24. The compound of claim 1 which is 4-(2,3-dichlorophenyl)-1,4,5,6,7,8-hexahydro-2-methyl-5-oxo-1,7-naphthyridine-3-carboxylic acid 2-phenoxyethyl ester, hydrochloride or a pharmaceutically acceptable salt thereof.

25. The compound of claim 1 which is 1,4,5,6,7,8-hexahydro-2-methyl-5-oxo-4-(pentafluorophenyl)-1,7-naphthyridine-3-carboxylic acid 2-methyl-2-phenoxypropyl ester, hydrochloride or a pharmaceutically acceptable salt thereof.

26. The compound of claim 1 which is 1,4,5,6,7,8-hexahydro-2-methyl-5-oxo-4-(pentafluorophenyl)-1,7-naphthyridine-3-carboxylic acid 4-phenoxybutyl ester or a pharmaceutically acceptable salt thereof.

27. The compound of claim 1 which is 1,4,5,6,7,8-hexahydro-2-methyl-5-oxo-4-(pentafluorophenyl)-1,7-naphthyridine-3-carboxylic acid 2-(2,3-dichlorophenoxy)ethyl ester or a pharmaceutically acceptable salt thereof.

28. The compound of claim 1 which is 4-(2-chloro-6-fluoro-3-methylphenyl)-1,4,5,6,7,8-hexahydro-2-methyl-5-oxo-1,7-naphthyridine-3-carboxylic acid 2-phenoxyethyl ester or a pharmaceutically acceptable salt thereof.

29. The compound of claim 1 which is 4-(2,3-dichloro-6-fluorophenyl)-1,4,5,6,7,8-hexahydro-2-methyl-5-oxo-1,7-naphthyridine-3-carboxylic acid 2-phenoxyethyl ester or a pharmaceutically acceptable salt thereof.

* * * * *